United States Patent
D'Alessandro

(10) Patent No.: US 11,164,670 B2
(45) Date of Patent: Nov. 2, 2021

(54) METHODS AND APPARATUS FOR IDENTIFYING SKIN FEATURES OF INTEREST

(71) Applicant: Canfield Scientific, Incorporated, Fairfield, NJ (US)

(72) Inventor: Brian D'Alessandro, Wayne, NJ (US)

(73) Assignee: Canfield Scientific, Incorporated, Parsippany, NJ (US)

(*) Notice: Subject to any disclaimer, the term of this patent is extended or adjusted under 35 U.S.C. 154(b) by 696 days.

(21) Appl. No.: 15/074,304

(22) Filed: Mar. 18, 2016

(65) Prior Publication Data

US 2016/0275681 A1    Sep. 22, 2016

Related U.S. Application Data

(60) Provisional application No. 62/134,830, filed on Mar. 18, 2015.

(51) Int. Cl.
*G06T 15/08* (2011.01)
*G16H 30/20* (2018.01)
(Continued)

(52) U.S. Cl.
CPC ........... *G16H 30/20* (2018.01); *A61B 5/1032* (2013.01); *A61B 5/441* (2013.01); *A61B 5/444* (2013.01); *A61B 5/7425* (2013.01); *G06T 3/4038* (2013.01); *G06T 5/001* (2013.01); *G06T 7/0016* (2013.01); *G06T 15/08* (2013.01); *G16H 30/40* (2018.01); *G16H 50/20* (2018.01);
(Continued)

(58) Field of Classification Search
CPC ..... G06T 7/0016; G06T 3/4038; G06T 15/08; G06T 2200/32; G06T 2200/04; G06T 2207/30088
See application file for complete search history.

(56) References Cited

U.S. PATENT DOCUMENTS 6,993,167 B1 * 1/2006 Skladnev ............. A61B 5/0059
382/128
7,415,143 B2 * 8/2008 Grichnik ............... A61B 5/415
382/128
(Continued)

FOREIGN PATENT DOCUMENTS

WO          97/47235 A1     12/1997
WO     WO-9747235 A1 *    12/1997    ........... A61B 5/0059

OTHER PUBLICATIONS

International Search Report and Written Opinion of the ISA, PCT/US2016/023159, dated Jun. 6, 2016.

*Primary Examiner* — Shawn S An

(57) ABSTRACT

Methods and apparatus are disclosed that assist a user such as a doctor in examining large areas of skin quickly and effectively by determining an attribute associated with each of a plurality of skin features included in one or more images of skin; generating a tile image of each of the plurality of skin features; arranging the tile images in accordance with the attribute associated with each of the plurality of skin features; and controlling a display device to display the tile images of the plurality of skin features. Advantageously, systems and methods according to the present disclosure enable the organization and presentation of large sets of visual as well as non-visual data that can be readily navigated and assimilated by the user.

28 Claims, 6 Drawing Sheets

(51) Int. Cl.

| | |
|---|---|
| *A61B 5/103* | (2006.01) |
| *A61B 5/00* | (2006.01) |
| *G06T 5/00* | (2006.01) |
| *G16H 30/40* | (2018.01) |
| *G16H 50/50* | (2018.01) |
| *G16H 50/20* | (2018.01) |
| *G06T 3/40* | (2006.01) |
| *G06T 7/00* | (2017.01) |

(52) U.S. Cl.
CPC .......... *G16H 50/50* (2018.01); *A61B 2576/00* (2013.01); *G06T 2200/04* (2013.01); *G06T 2200/32* (2013.01); *G06T 2207/10024* (2013.01); *G06T 2207/30088* (2013.01)

(56) References Cited

U.S. PATENT DOCUMENTS

| | | | |
|---|---|---|---|
| 2009/0028380 A1* | 1/2009 | Hillebrand | G06T 11/60 |
| | | | 382/100 |
| 2009/0082637 A1 | 3/2009 | Galperin | |
| 2009/0118600 A1* | 5/2009 | Ortiz | A61B 5/0064 |
| | | | 600/306 |
| 2009/0327890 A1 | 12/2009 | Mertz et al. | |
| 2012/0238863 A1 | 9/2012 | Cha et al. | |
| 2013/0245400 A1* | 9/2013 | Kuo | A61B 5/1032 |
| | | | 600/306 |
| 2014/0016832 A1* | 1/2014 | Kong | A61B 5/1128 |
| | | | 382/115 |
| 2014/0043458 A1 | 2/2014 | Cha et al. | |
| 2014/0126787 A1* | 5/2014 | Zuhlke Kimball | G06T 7/0012 |
| | | | 382/128 |

* cited by examiner

METHODS AND APPARATUS FOR IDENTIFYING SKIN FEATURES OF INTEREST

RELATED APPLICATIONS

This Application claims priority from U.S. Provisional Patent Application No. 62/134,830, filed Mar. 18, 2015 and incorporated herein by reference in its entirety.

BACKGROUND INFORMATION

For individuals having a high-risk for skin conditions such as melanoma, a full body examination of their skin is oftentimes performed in order to identify features, for example, lesions, warranting further consideration. Traditionally, a physician such as a dermatologist or other health care practitioner, will visually inspect areas of the individual's skin looking for interesting or suspicious lesions and in particular so-called "ugly duckling" lesions that do not resemble neighboring lesions. The practitioner may then more closely inspect particular lesions with an instrument such as a dermatoscope.

As may be readily appreciated, keeping track of lesions viewed, their locations, shapes, sizes and other relevant attributes is a complex and time consuming task—especially for individuals (i.e., patients) having a large number of lesions—as it may require the practitioner to frequently make measurements and take notes as the lesions are viewed individually, one-by-one. Notably, these same issues may arise when examining numerous other skin features of interest such as acne, rosacea, pores, scars, sores, bruises, etc.

More recently, high-resolution, full body, three-dimensional (3D) photographic imaging systems and methods have been proven to effectively capture a visual 3D record of a patient's entire skin area. Notwithstanding the considerable utility of such 3D systems and methods, the complex and time consuming process of manually inspecting a patient's skin—or a 3D model of the patient's skin—and then marking, measuring and tagging any interesting and/or suspicious features still remains.

Operationally, a 3D photographic system such as the Canfield Scientific VECTRA WB360 whole body imaging system, utilizes multiple stereo pairs of cameras positioned around a body or a portion thereof to capture multiple images simultaneously. The multiple captured images are stitched together to construct a 3D model of the body or a portion thereof that is imaged. The system allows a user, such as a dermatologist, to rotate, zoom, and pan around the 3D model. Alternatively, a "body map" made up of a set of two-dimensional (2D) images may also be used, even without 3D reconstruction. While viewing the reconstructed 3D model or 2D map, the system allows the user to manually tag displayed features of interest, such as with a pointing device like a mouse. Once tagged, a circle is displayed on top of the tagged feature and written notes can be added. Features may also be linked (associated) with close-up dermoscopy images taken separately with, for example, a handheld device. Selecting a tagged lesion with a mouse or other input device will make any such associated dermoscopy images visible on screen.

As may be readily appreciated by those skilled in the art, such systems provide the benefit of generating an examination record of all or large portions of a patient's skin that can be reviewed at a later time, for example, after the patient has left the practitioner's office.

While such state-of-the-art, whole-body 3D photographic systems represent a significant improvement over traditional, in-person skin inspections, they nevertheless lack automated detection or measurement of skin lesions and a way of consolidating or summarizing visual data embedded in the images as well as any additional data that may be captured in the course of performing an examination.

Such limitations are particularly acute when, for example, there are many skin features to be inspected and it is difficult for a practitioner to focus on any details of an individual feature, while ignoring everything else that is visible in a system display. Notably with such systems, when their display is widely zoomed-out, all features may be visible but details of individual features may not be seen. Conversely, when the displays of such systems are narrowly zoomed-in for an up-close view of a particular feature or region, an individual feature's details may be inspected, but other features which are outside the field of view of the current zoom-level are not visible, and therefore cannot be easily compared with those in the field of view.

Accordingly, methods and apparatus that facilitate a practitioner to expeditiously, efficiently and effectively identify, isolate and compare skin features of interest from an otherwise overwhelming number of skin features, would represent an advance in the art.

SUMMARY OF THE DISCLOSURE

Problems such as those described above are solved and an advance is made in the art according to an aspect of the present disclosure directed to a method that assists a user in examining large areas of skin quickly and effectively by: determining at least one attribute associated with each of a plurality of skin features included in one or more images of skin; generating a tile image of each of the plurality of skin features; arranging the tile images in accordance with the at least one attribute associated with each of the plurality of skin features; and controlling a display device to display the tile images of the plurality of skin features.

Additionally, an advance is made in the art according to an aspect of the present disclosure directed to an apparatus that comprises a storage device containing instructions; and a processor executing the instructions to: determine at least one attribute associated with each of a plurality of skin features included in one or more images of skin; generate a tile image of each of the plurality of skin features; arrange the tile images in accordance with the at least one attribute associated with each of the plurality of skin features; and control a display device to display the tile images of the plurality of skin features.

Advantageously—and in sharp contrast to the prior art—apparatus and methods according to the present disclosure enable the organization and presentation of large sets of visual as well as non-visual data that can be readily navigated and assimilated by the user.

These and other aspects of the present disclosure and exemplary variants thereof are described in greater detail below.

BRIEF DESCRIPTION OF THE DRAWINGS

A more complete understanding of the present disclosure may be realized by reference to the accompanying drawing in which.

DETAILED DESCRIPTION

Figure 1:
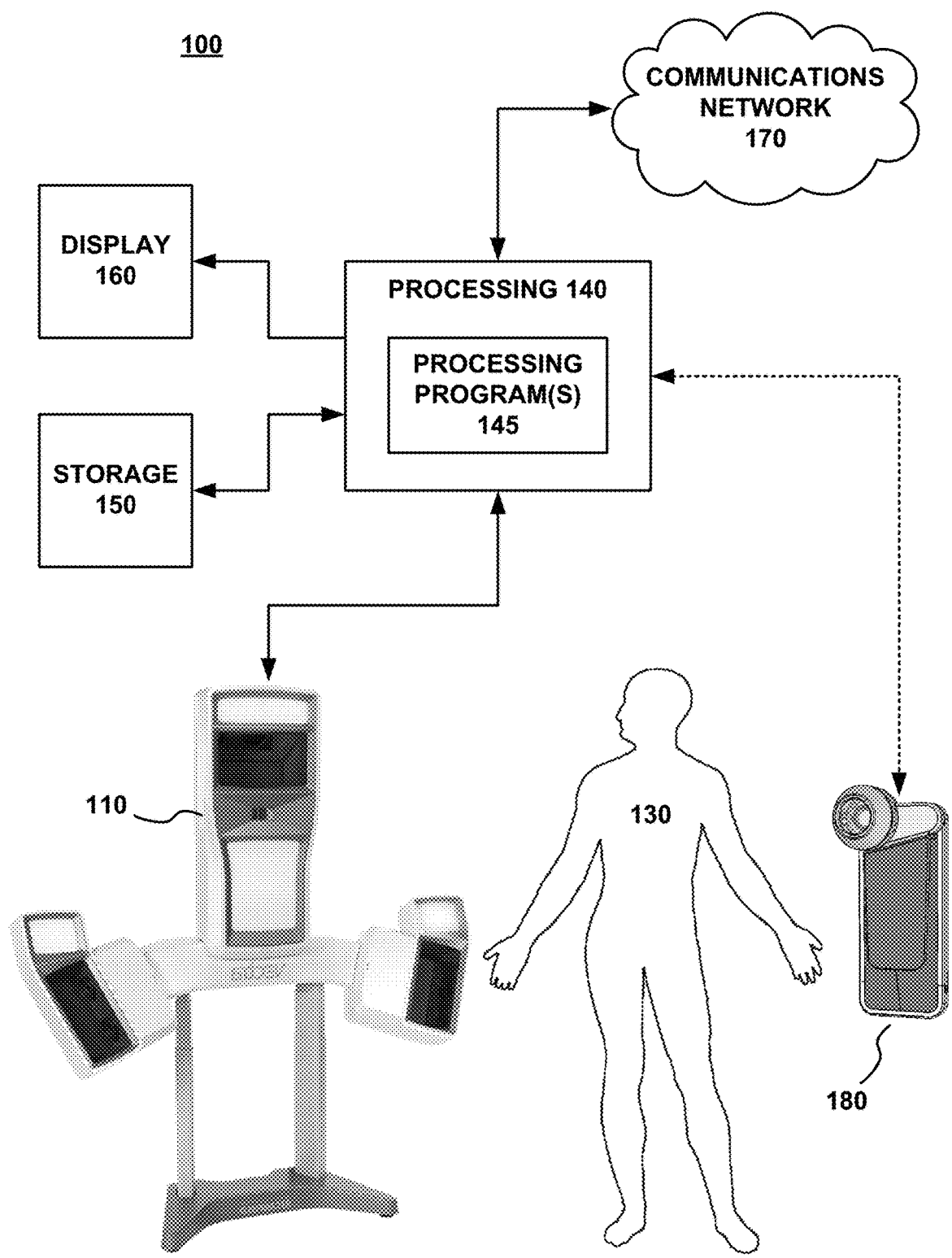
FIG. 1 is a schematic representation of an exemplary system in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not be shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the Figures, including any functional blocks labeled as "processors" or "processing", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

Turning now to FIG. 1, there is shown in schematic form an exemplary system 100 for capturing and processing images according to an aspect of the present disclosure. As shown in FIG. 1, components of system 100 include an image capture system 110 coupled to a processing module 140. Image capture system 110 may include 2D or 3D image capture element(s) for capturing one or more images of all or a portion of a subject 130. Advantageously, the captured images can be single mode or multimodal—including, for example, those from standard white light, polarized light, and/or fluorescent light—captured at selected wavelengths and/or illuminated with selected wavelengths of light.

Images captured by image capture system 110 are provided to processing module 140 for processing as described in greater detail below. Of further advantage, processing module 140 may also control image capture system 110, for example, by controlling particular aspects of the image capture and/or illumination of subject 130.

As depicted in FIG. 1, image capture system 110 may include one or more illumination sources that when activated illuminate subject 130. Such illumination may advantageously include one or more respective filtering element(s). Light reflected or emitted from subject 130 positioned appropriately may be captured by system 110 including one or more filtering elements (not specifically shown), which may include one or more filters for passing or blocking light of a selected wavelength or band of wavelengths, and/or polarizers, (which are referred to herein collectively as "filters") which can be selectively placed in or out of a respective optical path of the filtering element. As implied earlier, we note that the term "light" as used herein is not necessarily limited to electromagnetic radiation that is humanly visible. Notably, light as used herein refers to electromagnetic radiation in any portion of the electromagnetic spectrum including that above and/or below and/or within the range of human vision.

Returning to our discussion of FIG. 1, we note that processing module 140 may be implemented, for example, with one or more computers, workstations, or the like, operating in accordance with one or more programs 145 embodied in a compatible machine-readable medium. As readily understood by those skilled in the art, processing module 140 may be coupled to storage module(s) 150 and display module(s) 160 as implementation requirements dictate. Processing module 140 may also be connected to a communications network 170, such as the Internet, for transmitting images and/or data, and/or receiving commands, software updates or the like.

System 100 may also include or otherwise interact with additional instrumentation such as dermatoscope 180, which can be used to capture close-up images of skin areas or skin features of interest on subject 130. Advantageously, such images can then be associated with corresponding images captured by image capture system 110 and/or with features identified therein.

A communications link between processing module 140 and dermatoscope 180 (or other instrumentation not specifically shown) may be wired or wireless, and may be direct (such as over a Bluetooth or USB connection directly between processing module 140 and dermatoscope 180) or indirect, such as via communications network 170, among other possibilities.

Along with images, dermatoscope 180 can provide metadata associated with the images, such as, for example, gyroscope/positional data of dermatoscope 180 which could help determine the orientation of captured dermatoscopy images with respect to the subject. It may also be possible, particularly with a device having processing capabilities, for dermatoscope 180 to also perform some pre-processing of the images that it provides to processing module 140.

Also, as mentioned, other instrumentation can interact with processing module 140 to provide both image and other data including close-up image capture systems such as confocal microscopy systems, optical coherence tomography (OCT) systems, and colorimeters, among others.

In one illustrative implementation, image capture system 110 is one of the family of VECTRA imaging systems from Canfield Scientific, Inc. (e.g., a VECTRA WB180, WB360 or H1 imaging system) and dermatoscope 180 is a VEOS dermatoscope, also from Canfield Scientific, Inc.

It should be noted that the exemplary system 100 illustrates just one of a variety of possible arrangements contemplated by the present disclosure. For example, the various modules of system 100 need not be co-located. For example, image capture system 110 and display module 160 can be located in a dermatologist's office and processing module 140 and storage module 150 can be remotely located, or "cloud-based," interacting with image capture system 110 and display module 160 over communications network 170. In other exemplary arrangements, display module 160 can be remotely located from image capture system 110, thereby allowing a dermatologist at display module 160 to remotely examine a subject's skin.

Figure 2:
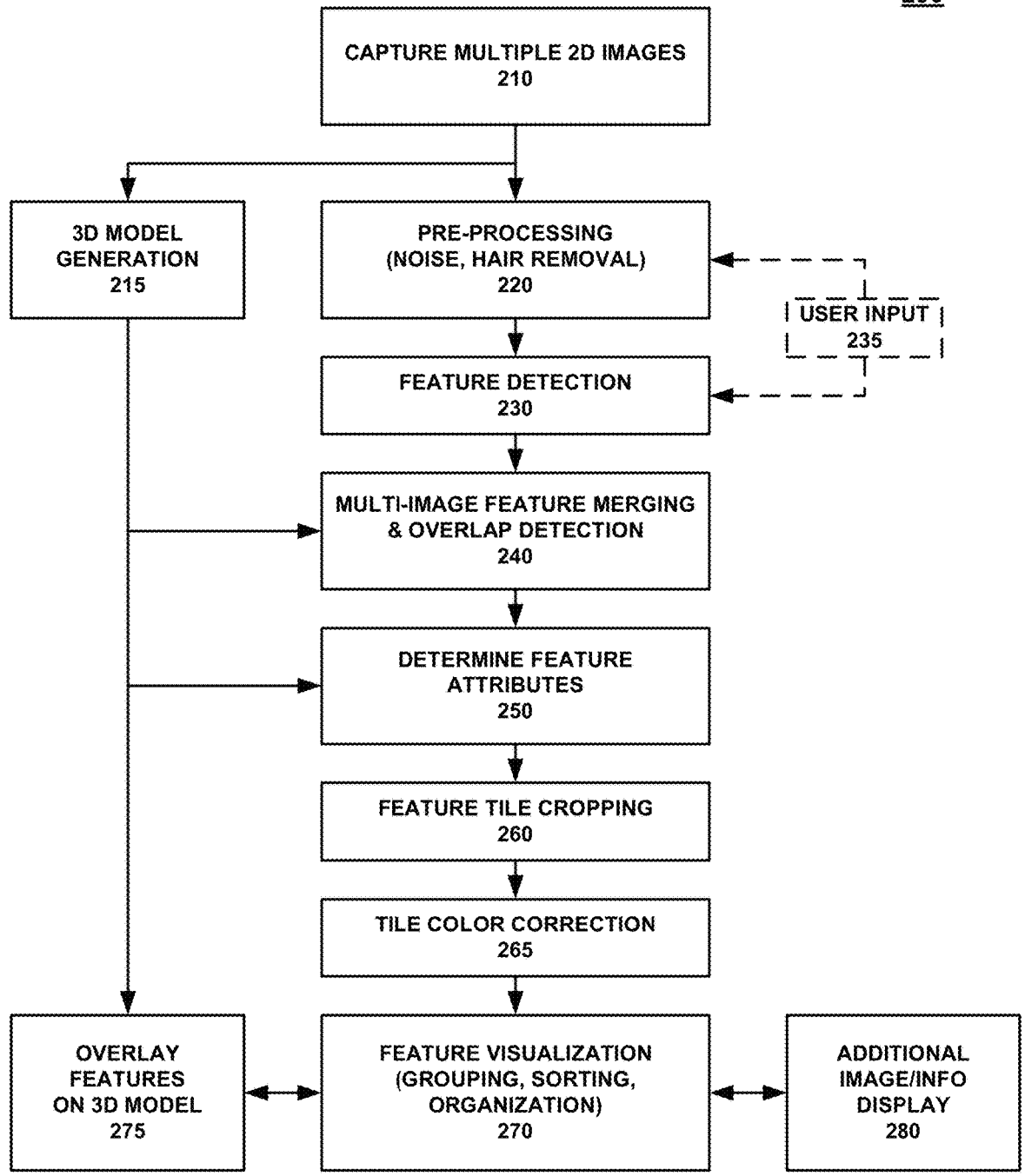
FIG. 2 is a flow chart depicting an exemplary method in accordance with the present disclosure.

Turning now to FIG. 2, there is shown a high-level flow chart of an illustrative method 200 of processing images according to aspects of the present disclosure. As will be readily understood by those skilled in the art, the method 200 can be carried out, for example, using system 100 of FIG. 1, wherein processing module 140 thereof operates in accordance with processing program(s) 145.

As shown in FIG. 2, and with simultaneous reference to system 100 of FIG. 1, the illustrative method 200 begins at step 210 in which multiple 2D images of subject 130 (whole body or a portion thereof) are captured by image capture system 110. In addition to being stitched together to generate a 3D model of the subject at step 215, the 2D images are processed and analyzed to detect skin features of interest. The detected skin features are projected onto the 3D model of the subject and conformed to the shape thereof. Alternatively, in a 2D capture system implementation, the features are projected onto the 2D images of a body map.

In an illustrative implementation, multiple 2D images are synchronously captured to reconstruct a 3D model of the subject being imaged. Every pixel in every source image can thus be mapped to real world x, y, z coordinates in 3D space. Notably, this is important for dealing with overlapping 2D images as well as for accurate dimensional measurements across the subject, and thus, for each feature.

The captured 2D images are used to detect skin features. Advantageously, such feature detection may be performed through image processing algorithms that automatically segment boundaries of the detected features, or through varying degrees of user involvement, with or without practitioner overview. In illustrative method 200, feature detection is performed at step 230, which preferably includes or is preceded by a preprocessing or filtering step 220 to remove noise or other interfering elements captured in the image, such as hair, which could otherwise adversely affect segmentation.

In exemplary embodiments, filtering 220 and/or feature detection 230 may be selectively performed in response to user input 235. For example, detection threshold values used by feature detection 230 can be changed by user input in order to more finely control the relative sensitivity and specificity of the feature detection. As may be readily appreciated, some users may choose to increase the sensitivity in order to increase true positives, while others may want to decrease the sensitivity so as to reduce false positives. In this way, a user desiring a non-default functionality can adjust the thresholds as desired. Additionally, in exemplary embodiments, a user may also have the ability to manually delete detected features, if some have been wrongly detected, such as due to noise, or even re-draw the segmented feature boundary. If a feature has its boundary redrawn, any of its measurements or metrics affected thereby are preferably regenerated based on the revised boundary, likewise updating any visualization displays containing that feature.

Features detected in overlapping areas between or among multiple images are merged at step 240 to ensure that individual features captured in multiple images are not duplicatively reported. This can be done using any suitable method of image correspondence, including involving the 3D model, if available.

In an exemplary implementation, generation of the 3D model at step 215 includes the generation of a set of non-overlapping masks corresponding to a set of captured 2D images. Once segmentation is performed in step 230 on each 2D image in its entirety, the corresponding masks are applied in step 240 to eliminate any overlap.

Alternatively, images produced by a camera positioned at the best angle to view a particular area of the skin can be selected for the segmentation of features within that area. In this case, any given area is analyzed once, specifically, within the image that provides the best view of that area. Overlapping areas in other images which are not as optimal are ignored.

As a further alternative, features can be detected in all of the 2D images, regardless of the view, and then re-projected into other images based on pixel-to-3D coordinate mappings, while keeping the union, intersection, or some other suitable combination of the segmented feature areas.

At step 250, for each detected feature a set of one or more attributes describing that detected feature may be determined, such as, for example, size (e.g., area, diameter, major/minor axis length, perimeter), intensity, color (e.g. average RGB or L*a*b* values, average delta RGB or L*a*b* values relative to the local background skin color), symmetry, border irregularity, circularity, eccentricity, location (e.g., x, y, z coordinates in real world space, anatomical body part such as head, neck, front or back torso, the left or right arm, etc.), a derived measure, such as "pathological significance," or a pathological classification, among other possibilities. For any attribute that pertains to a physical measurement, such as area, length, width, etc., the actual pixel-based measurement from the 2D image is preferably converted into a physical measurement (such as in inches, or millimeters, etc.) using spatial information such as from a ruler or other reference object of known size appearing in the image. In the case of 3D photography, such information can be derived from a calibrated 3D model reconstruction.

Advantageously, information from the 3D model allows features to be corrected for perspective distortion from the 2D projection—which is noticeable around curved surfaces—prior to calculating their attributes. This allows for very accurate measurements, despite dealing with 2D images which are not captured perpendicular to the subject's surface, or in which the number of pixels per inch (PPI) can vary even within the same image due to different areas of the subject being located at different positions and distances away from the camera.

At step 260, the detected features can then be isolated, or cropped out of the original 2D images to create a tile or thumbnail view of each feature. Perspective correction may also be applied to these tiles, if available, so the tiles appear as if they were captured perpendicular to the feature. Tiles may be cropped into a square, circle, rectangle, hexagon, or any other suitable shape.

At step 265, the skin feature tiles may be color corrected to normalize the subject's background skin surrounding the skin features. In performing such a color correction, first, an estimate of the subject's overall skin color may be computed from the original captured images. Next, the area of background skin within each cropped tile (outside the detected feature boundary) may be used to compute a color correction function for that entire tile with respect to the subject's skin color estimate. For example, each tile could be shifted in L*a*b* color space such that the delta between the subject's skin color and the tile's background skin color averages to zero. Alternatively, each tile may be color corrected by a calculated or fixed amount based on the distance or position of the feature in the tile with respect to the positioning of the flashes, camera, and/or ambient light sources. For example, features closer to a flash could be darkened while features further away from a flash could be brightened. A benefit of color correcting the tiles individually with respect to the subject's skin color is greater consistency of visualization. A viewer may be distracted by intensity shifts in cropped tiles due to factors such as distance from ambient light sources, flashes, or even tanning. However, by normalizing the background skin color of each tile, the skin features themselves can be more easily compared from one location to another.

Figure 3:
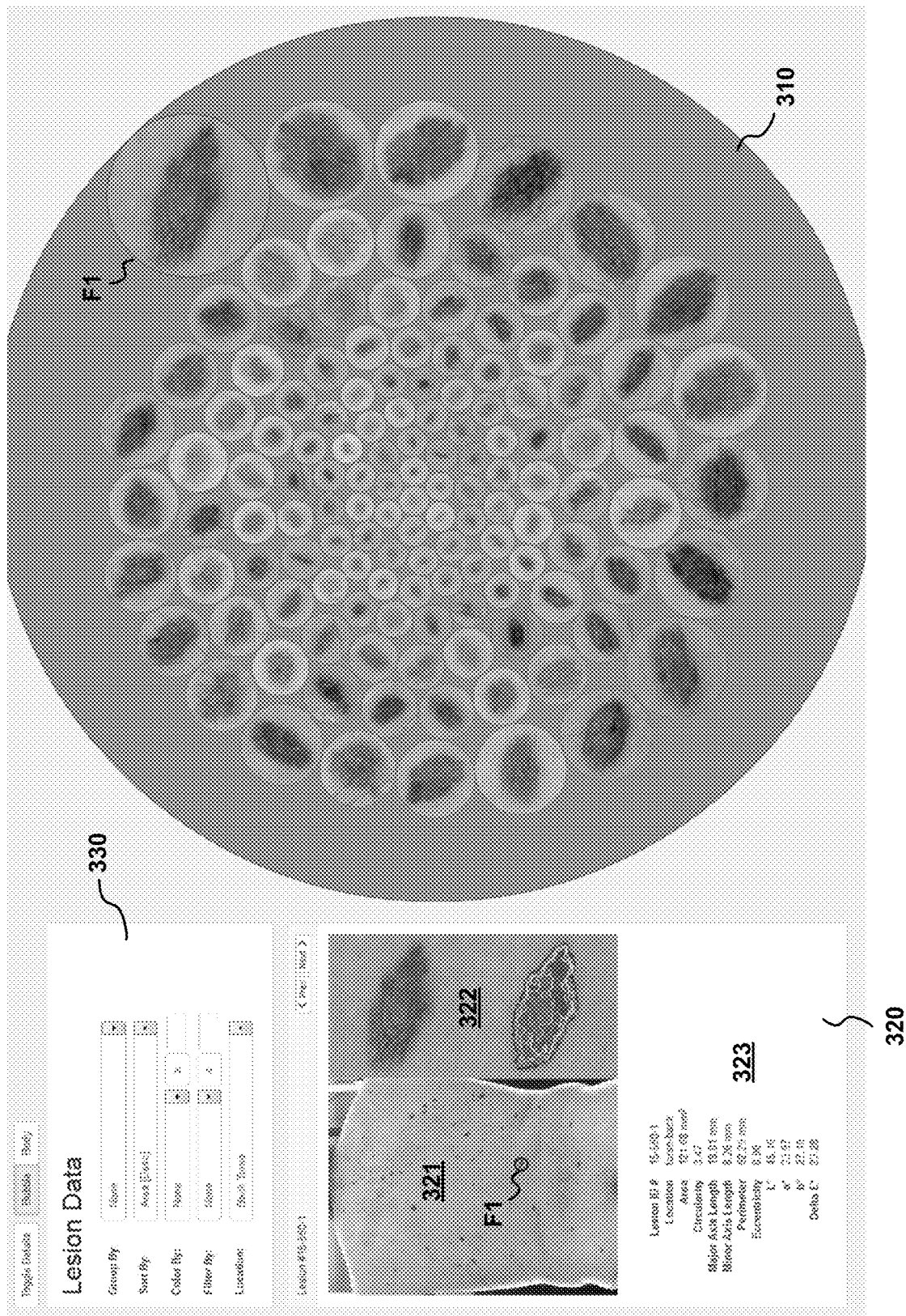
FIG. 3 is an illustrative view of a visualization scheme implemented with embodiments of the present disclosure.
Figure 4:
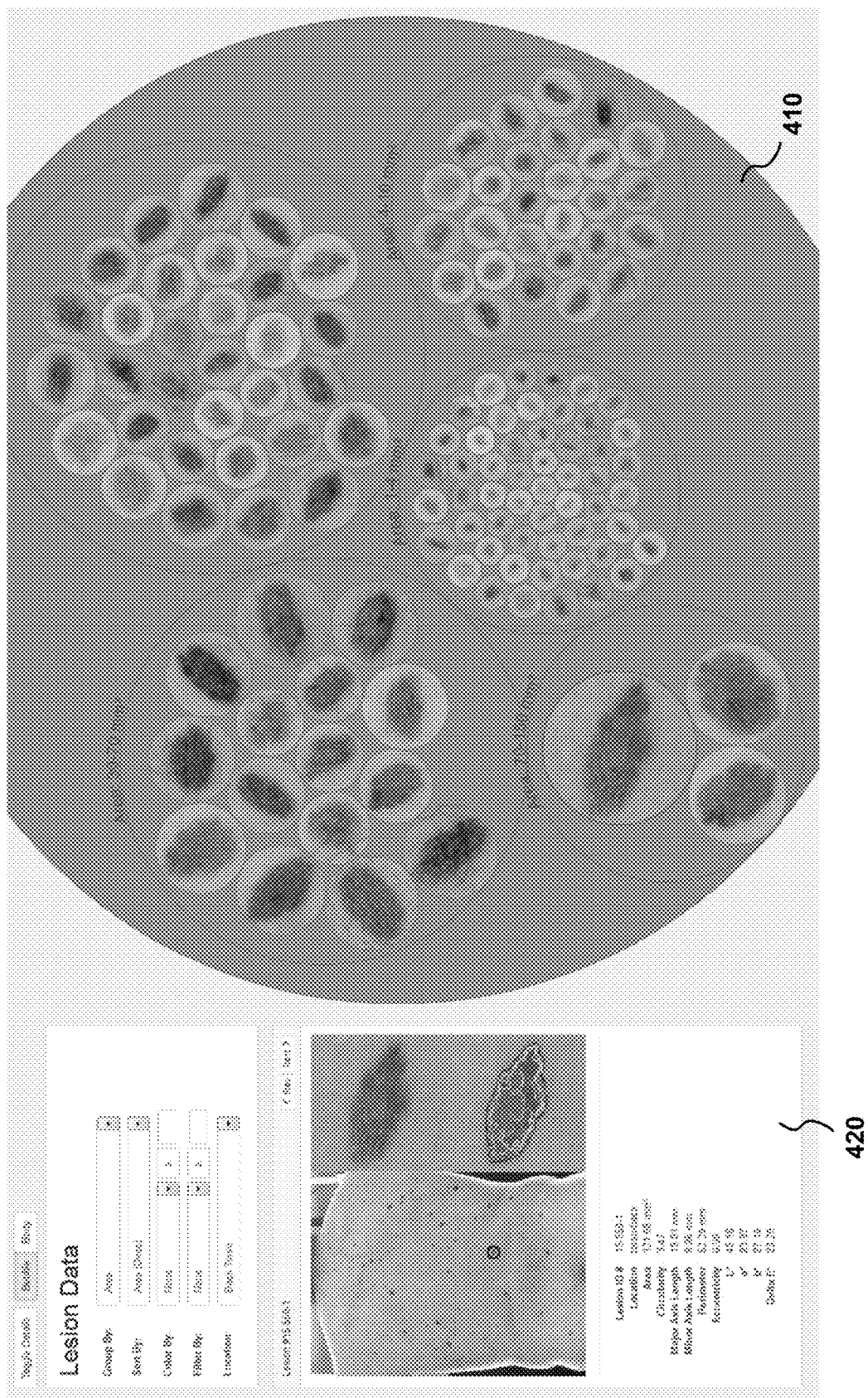
FIG. 4 is a further illustrative view of a visualization scheme implemented with embodiments of the present disclosure.

At step 270, the tiles generated in step 260 are arranged in a visualization or display scheme to allow an easy, at-a-glance overview of visual aspects of the features represented by the tiles all at once. Illustrative views of such a visualization scheme are shown in FIG. 3 and FIG. 4. Advantageously, tiles can be square, circular, hexagonal, or any other suitable shape, and can be arranged together in a grid, row, column, spiral, tree, or any other suitable layout format, as shown in FIGS. 3 and 4 at 310 and 410, respectively. Additionally, the tiles can be sorted or ordered according to one or more attributes or combinations thereof. For example, in the illustrative arrangement shown in FIG. 3, circular tiles of detected lesions are arranged in a spiral in order of area.

The tiles can also be grouped according to one or more attributes of the features shown in the tiles or divided into groups based on a set of criteria or thresholds for one or more attributes. These groups could then be arranged together on a display, allowing a viewer to appreciate which features have similar attributes and which ones may be outliers.

In the illustrative arrangement of FIG. 4, tiles of the same detected lesions shown in FIG. 3 are arranged in groups defined by ranges of area. These groups can also be arranged in a hierarchy of any number of levels, with each lower level dividing the parent based on one or more feature attributes. Thus, for example, each of the groups shown in FIG. 4 can be further divided into sub-groups based on—for example—color, border regularity, body location, or any other suitable attribute. Features located across the entire body can be grouped together, or they can be organized by grouping sections of the body, such as the face, torso, legs, arms, etc.

A system according to the present disclosure preferably allows a user to control one or more settings affecting the presentation of features, such as those illustrated in FIGS. 3 and 4. Preferably, the user can select one or more filters for application on the feature attributes to narrow down the features to a subset in which the user may be particularly interested. For example, the user could select only those features on the left arm which have an area greater than 5 mm$^2$. In response, the system would then update the visualization displayed to show, or highlight, only the features which meet those criteria.

The location of the detected features (such as centroid position or boundary, etc.) can be projected back onto the original 2D images or 3D model, at step 275, for an interactive view of the subject with the detected features. This can be done before or after the above-described selective filtering. Such views are illustrated in FIGS. 3 and 4, at 320 and 420, respectively.

Advantageously, features projected back onto the original 2D images or 3D model can be optionally color coded according to one or more attributes of each feature. In this way, a user can visualize the true positioning of the features and how the features actually appear on the subject, along with additional annotated information to assist them in ascribing meaning to what they see and identifying the most interesting features. These features can also be tagged for capture with an alternate image capture system, such as dermoscopy, confocal microscopy, optical coherence tomography (OCT), or other close-up image capture system. Once these additional images are captured, they can be linked, at step 280, with their respective features, enabling the user to easily highlight a feature and view its additional information and images in a consolidated manner. Such additional images and information are shown in FIGS. 3 and 4, at 320 and 420, respectively.

As shown in FIGS. 3 and 4, information relating to individual features can be displayed at 320 and 420. FIG. 3 shows the illustrative case of a feature F1, which is highlighted in display area 310 and for which additional information is presented in display area 320. Feature F1 can be selected, for example, by a user clicking or otherwise selecting the tile displayed in area 310 for feature F1.

In the exemplary embodiment shown in FIG. 3, display area 320 includes portions 321-323. Display portion 321 displays an image of the part of the body in which feature F1 is found, which in this case is the back torso, with feature F1 highlighted, such as by a circle or other suitable means allowing a user to readily locate feature F1 within the image.

Display portion 322 displays one or more close-up images of feature F1 by itself. As shown in FIG. 3, display portion 322 includes a conventional reflectance image of feature F1, as well as a version of the image with additional graphical information superimposed thereon, in this case, a contour map in which the contour lines represent varying levels of intensity (L*) within the feature. Additional images of feature F1 captured, for example, in a variety of modalities (e.g., polarized, UV) and/or at different times can also be displayed. The close-up image(s) displayed in portion 322 may be obtained from the original image of the body part or whole body or from other sources, such as dermatoscope 180 shown in FIG. 1.

Portion 323 of display area 320 includes alphanumeric information relating to feature F1, such as, for example, an ID, location, size metrics (e.g., area, major and minor axis lengths, perimeter), shape metrics (e.g., circularity, eccentricity), and color information (e.g., average L*a*b* values within the feature, delta E*). Delta E* can be computed by:

$$\Delta E^* = \sqrt{(L^*_F - L^*_S)^2 + (a^*_F - a^*_S)^2 + (b^*_F - b^*_S)^2}$$

where $L^*_F$, $a^*_F$, and $b^*_F$ represent the average L*a*b* values of the feature, and $L^*_S$, $a^*_S$, and $b^*_S$ represent the average L*a*b* values of the local background skin inside the tile but outside the feature.

Figure 5:
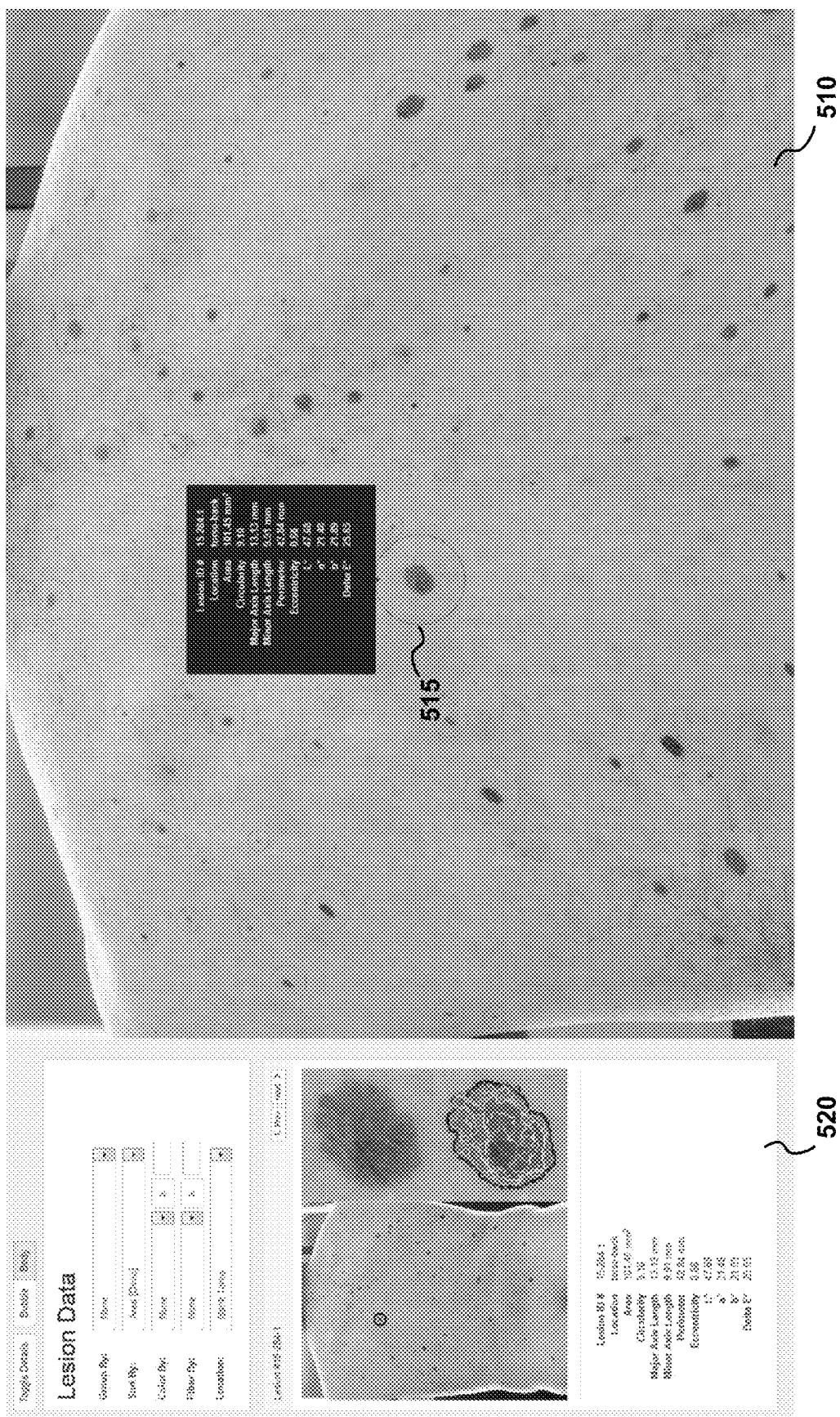
FIG. 5 is a further illustrative view of a visualization scheme implemented with embodiments of the present disclosure.

In addition to the views such as those shown at 310 and 410 in FIGS. 3 and 4, an exemplary system according to the present disclosure can display a whole or partial body view, such as shown in FIG. 5 at 510. In such a view, the system can provide a hover tool 515 that a user can move to any displayed feature in order to view information relating to the feature. An enlarged view of the feature can be viewed within the hover tool, thereby simulating a loupe or the like, and/or within an area 520. Alphanumeric information relating to the feature can be provided proximate to the hover tool and/or within area 520. The views of FIG. 5 are also useful for embodiments in which the system can bypass the generation, arrangement and display of arranged feature tiles (as shown in FIGS. 3 and 4) and instead indicate one or more selected features of interest directly on the whole or partial body view shown at 510 and/or 520. The features of interest can be selected based on one or more attributes, such as for example, those features having a pathological significance greater than a threshold value. The skin feature(s) meeting the selection criteria can be displayed by the system with some indication or otherwise highlighted, such as by a circle or other suitable indicator allowing a user to readily locate the feature(s) within the image. As such, skin features are automatically detected; one or more of their attributes determined (e.g., measured, classified); one or more of the detected skin features selected based on the one or more attributes; and the selected skin features, ostensibly those warranting further consideration, are flagged to bring them to the user's attention.

For features for which information is available from multiple points in time, such as for example, two or more images or image sets captured at different timepoints, detected features can be tracked from one timepoint to another through a variety of methods such as image registration, or feature descriptor tracking. If the same feature can be located in one or more timepoints, any changes in measured attributes about the feature can be used to sort, group, or filter the visualization scheme. For example, changes in area of selected pigmented lesions over the course of a given period of time can be determined and used to generate a spiral diagram, such as that of 310, in which the lesions are ordered by the percent increase in area. Such a display enables a user to quickly see which lesions have had the most growth over a period of time, thereby warranting closer inspection. As such, in addition to arranging the tiles of features in accordance with one or more of their static attributes (i.e., attributes determined at a single timepoint), embodiments of the present disclosure also contemplate basing such arrangements in accordance with one or more dynamic attributes (e.g. changes or rates of change of attributes.)

Figure 6:
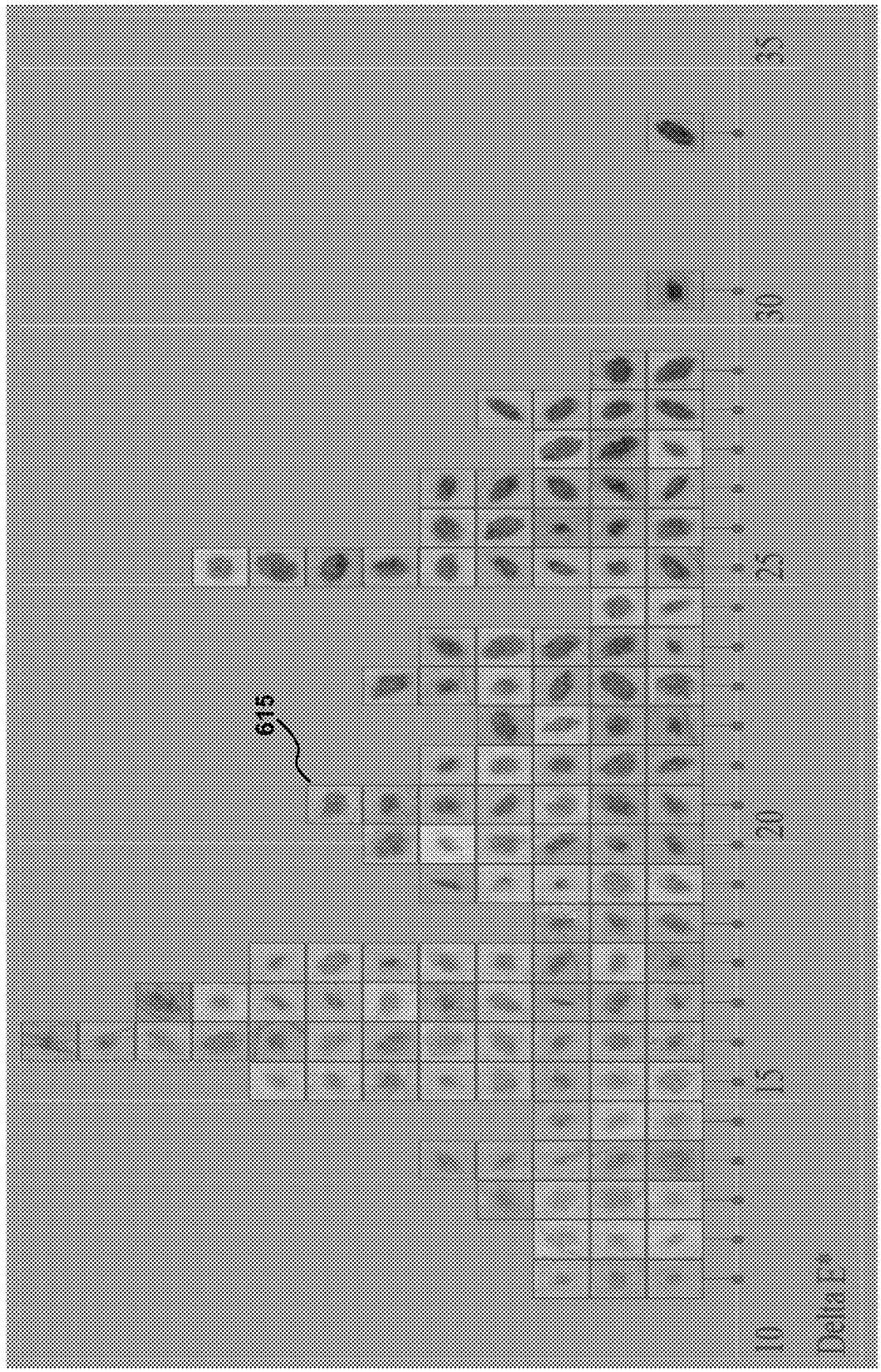
FIG. 6 is a further illustrative view of a visualization scheme implemented with embodiments of the present disclosure.

A further illustrative view of a visualization scheme implemented with embodiments of the present disclosure is shown in FIG. 6. As shown in FIG. 6, markers representing individual features are placed at their appropriate position on a fixed scale spanning the range of values for a feature attribute. In the exemplary display of FIG. 6, icons with feature image tiles 615 are arranged in a two-dimensional grid whose horizontal axis represents the color parameter ΔE relative to a background whose color is determined as an estimate of the subject's overall skin color. The vertical axis can represent another feature attribute, such as size, histogram bin count, or no other attribute. The exemplary display of FIG. 6 allows a user to readily see or otherwise visualize where clustering of attributes takes place, as well as the attribute values of outliers.

Before display in any visualization scheme (bubble/spiral diagram, histogram view, etc.), the feature tiles are preferably color corrected as described above with reference to FIG. 2.

In an exemplary embodiment, a map of features can be provided by system 100 to dermatoscope 180 to facilitate the location of those features for which additional images are to be captured with dermatoscope 180. The map can be displayed on dermatoscope 180 or on display 160 with features tagged for additional imaging being highlighted. As dermoscopic images are captured with dermatoscope 180, the images can be readily linked to the respective features and communicated to system 100.

As noted previously, one attribute of every feature is its anatomical location namely, the body part or region of the body where the feature is located. Such anatomical location information may be determined in a variety of manual or automated ways.

For example, for an image of an individual body part or region, features detected within the image are classified in accordance with the location on the body corresponding to that image; e.g., the body part location of a feature detected in an image of the left arm is determined to be the left arm. Such an association between the feature and the body part or location, may be made manually by a user.

Alternatively, the determination of the anatomical location(s) of features may be performed by an automated procedure. In one such procedure, an anterior or posterior silhouette projection of the body is input to a body part classification method. Such method may be advantageously implemented with, for example, a neural network trained to classify the boundary coordinates of the silhouette into their respective body parts, a rule-based set of heuristics (e.g., the legs are always below the torso for a standing subject), or a combination of techniques. Once major body parts have been identified and segmented, detected features may be re-projected and referenced against a body part map to automatically tag each feature with its anatomical location. Automated tagging techniques may also involve information from the 3D model, for example, the anterior or posterior regions may be distinguished by x, y, z coordinates of the feature relative to the known coronal plane, or by using the direction of the surface normal vector at the feature's location on the 3D model. Alternative tagging procedures may operate entirely in 3D, such as through dense correspondence matching.

At this point, while this disclosure has been presented using some specific examples, those skilled in the art will recognize that the teachings of this disclosure are not thus limited. Accordingly, this disclosure should be only limited by the scope of the claims attached hereto.

What is claimed:

1. A method performed by a skin imaging apparatus, comprising:
    determining at least one attribute associated with each of a plurality of skin features included in one or more images of skin;
    generating a plurality of tile images, each of the plurality of tile images generated being of each of the plurality of skin features, wherein generating the tile image of each skin feature includes cropping at least one of the one or more images of skin to isolate the skin feature from the other of the plurality of skin features;
    arranging the tile images in accordance with the at least one attribute associated with each of the plurality of skin features; and
    controlling a display device to display the arranged tile images of the plurality of skin features.

2. The method of claim 1, wherein the at least one attribute includes at least one of a size, shape, color, location, pathological significance, or pathological classification.

3. The method of claim 1 comprising performing a correction of the tile images, the correction including at least one of a color correction with respect to an overall skin color or a perspective correction.

4. The method of claim 1, wherein arranging includes at least one of sorting, grouping, or filtering the tile images.

5. The method of claim 1 comprising detecting each of the plurality of skin features in the one or more images of skin.

6. The method of claim 1 comprising processing the one or more images of skin, including performing at least one of a filtering, noise removal, or hair removal procedure.

7. The method of claim 1 comprising associating a tile image of a skin feature with an additional image of the skin feature, including at least one of a dermoscopy, confocal microscopy, or optical coherence tomography (OCT) image.

8. The method of claim 1 comprising generating a 3D model using the one or more images of skin, wherein controlling the display device includes controlling the display device to display one or more of the tile images on the 3D model.

9. The method of claim 1, wherein arranging the tile images includes arranging the tile images in two or more hierarchical levels, each successive level including two or more sub-groups of each group of tile images of a preceding level.

10. The method of claim 1 comprising associating one or more of the tile images with additional information related to the one or more skin features of said one or more tile images.

11. The method of claim 1 comprising controlling the display device to display the one or more images of skin with an indication for each of a selected one or more of the skin features.

12. A non-transitory computer-readable storage medium having stored thereon a computer program comprising instructions for causing a skin imaging apparatus to perform the method of claim 1.

13. The method of claim 1, wherein arranging the tile images includes arranging the tile images in a spiral or a histogram.

14. The method of claim 1, wherein arranging the tile images includes arranging the tile images so as to facilitate evaluation of the plurality of skin features.

15. The method of claim 1, wherein the at least one attribute includes a change or a rate of change in the at least one attribute.

16. A skin imaging apparatus comprising:
    a storage device containing instructions; and
    a processor executing the instructions to:
        determine at least one attribute associated with each of a plurality of skin features included in one or more images of skin;
        generate a plurality of tile images, each of the plurality of tile images generated being of each of the plurality of skin features, wherein generating the tile image of each skin feature includes cropping at least one of the one or more images of skin to isolate the skin feature from the other of the plurality of skin features;
        arrange the tile images in accordance with the at least one attribute associated with each of the plurality of skin features; and
        control a display device to display the arranged tile images of the plurality of skin features.

17. The apparatus of claim 16, wherein the at least one attribute includes at least one of a size, shape, color, location, or pathological significance.

18. The apparatus of claim 16, wherein the processor executes instructions to perform a correction of the tile images, the correction including at least one of a color correction with respect to an overall skin color or a perspective correction.

19. The apparatus of claim 16, wherein arranging includes at least one of sorting, grouping, or filtering the tile images.

20. The apparatus of claim 16, wherein the processor executes instructions to detect each of the plurality of skin features in the one or more images of skin.

21. The apparatus of claim 16, wherein the processor executes instructions to process the one or more images of skin, including performing at least one of a filtering, noise removal, or hair removal procedure.

22. The apparatus of claim 16, wherein the processor executes instructions to associate a tile image of a skin feature with an additional image of the skin feature, including at least one of a dermoscopy, confocal microscopy, or optical coherence tomography (OCT) image.

23. The apparatus of claim 16, wherein the processor executes instructions to:
    generate a 3D model using the one or more images of skin; and
    control the display device to display the 3D model with one or more of the tile images on the 3D model.

24. The apparatus of claim 16, wherein arranging the tile images includes arranging the tile images in two or more hierarchical levels, each successive level including two or more sub-groups of each group of tile images of a preceding level.

25. The apparatus of claim 16, wherein the processor executes instructions to associate one or more of the tile images with additional information related to the one or more features of said one or more tile images.

26. The apparatus of claim 16, wherein arranging the tile images includes arranging the tile images in a spiral or a histogram.

27. The apparatus of claim 16, wherein arranging the tile images includes arranging the tile images so as to facilitate evaluation of the plurality of skin features.

28. The apparatus of claim 16, wherein the at least one attribute includes a change or a rate of change in the at least one attribute.

* * * * *